US011197105B2

(12) United States Patent
Perscheid

(10) Patent No.: US 11,197,105 B2
(45) Date of Patent: Dec. 7, 2021

(54) VISUAL COMMUNICATION OF HEARING AID PATIENT-SPECIFIC CODED INFORMATION

(71) Applicant: IntriCon Corporation, Arden Hills, MN (US)

(72) Inventor: Andreas Perscheid, Ruedesheim (DE)

(73) Assignee: Intricon Corporation, Arden Hills, MN (US)

( * ) Notice: Subject to any disclaimer, the term of this patent is extended or adjusted under 35 U.S.C. 154(b) by 0 days.

(21) Appl. No.: 16/600,703

(22) Filed: Oct. 14, 2019

(65) Prior Publication Data
US 2020/0120430 A1 Apr. 16, 2020

Related U.S. Application Data

(60) Provisional application No. 62/745,085, filed on Oct. 12, 2018.

(51) Int. Cl.
*H04R 25/00* (2006.01)
*G06F 16/955* (2019.01)
*G16H 40/60* (2018.01)

(52) U.S. Cl.
CPC ......... *H04R 25/50* (2013.01); *G06F 16/9554* (2019.01); *G16H 40/60* (2018.01); *H04R 25/30* (2013.01); *H04R 25/554* (2013.01)

(58) Field of Classification Search
CPC ...... H04R 25/50; H04R 25/554; H04R 25/30; H04R 25/70; G06F 16/9554; G16H 40/60; G16H 10/60; G16H 40/67; G16H 40/40
See application file for complete search history.

(56) References Cited

U.S. PATENT DOCUMENTS

| 6,447,461 | B1 | 9/2002 | Eldon |
| 6,840,908 | B2 | 1/2005 | Edwards et al. |
| 7,024,000 | B1 | 4/2006 | Gabara et al. |
| 7,599,499 | B2 | 10/2009 | Naylor |
| 8,112,166 | B2 | 2/2012 | Pavlovic et al. |
| 8,135,138 | B2 | 3/2012 | Wessel et al. |
| 9,131,321 | B2 | 9/2015 | Sabin |

(Continued)

FOREIGN PATENT DOCUMENTS

DE 10147811 * 6/2003

*Primary Examiner* — Tuan D Nguyen
(74) *Attorney, Agent, or Firm* — Jeffrey D. Shewchuk; Shewchuk IP Services, LLC

(57) ABSTRACT

A method and system visually communicates hearing aid information between a patient's smartphone and an audiologist's computer system by using a QR code captured by a camera. When the audiologist's computer system takes a picture of the QR code on the display of the patient's smartphone, the QR code contains at least one piece of audiological data representing historical or current patient-specific usage of the hearing aid. When the patient's smartphone takes a picture of the QR code on the display of the audiologist's computer system, the QR code contains audiological data, which the patient's smartphone extracts to transmit instructions or information to adjust at least one audiological parameter setting on the patient's hearing aid. The patient may transmit or receive an image file of either QR code over a network, thereby communicating the same information with the audiologist.

17 Claims, 4 Drawing Sheets

(56) References Cited

U.S. PATENT DOCUMENTS

| | | |
|---|---|---|
| 9,319,812 B2 | 4/2016 | Banerjee et al. |
| 9,414,173 B1 | 8/2016 | Hou |
| 9,420,389 B2 | 8/2016 | Pontoppidan |
| 9,439,008 B2 | 9/2016 | Shennib |
| 9,445,754 B2 | 9/2016 | Schmitt |
| 9,468,401 B2 | 10/2016 | Van Hasselt et al. |
| 9,491,556 B2 | 11/2016 | Fitz et al. |
| 9,532,152 B2 | 12/2016 | Shennib |
| 9,699,576 B2 | 7/2017 | Wessel et al. |
| 9,782,131 B2 | 10/2017 | Van Hasselt et al. |
| 9,801,570 B2 | 10/2017 | Polley et al. |
| 9,946,842 B1 | 4/2018 | Stringham et al. |
| 10,185,834 B2 | 1/2019 | Adam et al. |
| 10,348,695 B1 | 7/2019 | Khassanov et al. |
| 10,424,031 B2 | 9/2019 | Neff |
| 2010/0196861 A1 | 8/2010 | Lunner |
| 2015/0296308 A1* | 10/2015 | Fluckiger ............ G06F 3/04842 715/733 |
| 2016/0166181 A1 | 6/2016 | Shennib |
| 2016/0212552 A1* | 7/2016 | Schneider ............... H04L 67/06 |
| 2017/0006389 A1* | 1/2017 | Pedersen ............. H04R 25/554 |

\* cited by examiner

VISUAL COMMUNICATION OF HEARING AID PATIENT-SPECIFIC CODED INFORMATION

CROSS-REFERENCE TO RELATED APPLICATION(S)

The present application claims the benefit of U.S. provisional patent application Ser. No. 62/745,085, filed Oct. 12, 2018. The contents of U.S. provisional patent application Ser. No. 62/745,085 is hereby incorporated by reference in entirety.

BACKGROUND OF THE INVENTION

Many people have some sort of hearing impairment, and are willing to wear a hearing aid or similar body-worn, battery-operated hearing assist device to address their hearing impairment. Such hearing aids not only amplify sound sensed from a microphone which is part of the device, but also are commonly modified to adjust or personalize the hearing aid audio output for the particular hearing profile of the patient. Being body-worn, typically in an exposed location on the head or ear of the patient, many hearing aid patients want their hearing aid to be relatively small and inconspicuous. In part due to size constraints, hearing aids typically do not include any visual display.

Many hearing aids, in addition to having a microphone to receive audible sound, also have an antenna or similar transceiver device/chipset to receive (and in many instances send) wireless signals. The wireless signals may include a) instructions about hearing aid settings, adjusting the way the hearing aid audio output is personalized for the hearing abilities/loss of that particular patient; and b) an audio stream to play audio from a source other than the microphone, such as playing a telephone call, a television program, or from a remote microphone. For example, U.S. Pat. No. 9,832,578 discloses a hearing aid which can receive audio streaming over a wireless proprietary audio streaming link and can also receive control data over a Bluetooth Low Energy ("BLE") link. U.S. Pat. No. 9,832,578 is owned by the assignee of the present invention and incorporated by reference, and summarized with reference to FIG. 1. As shown in FIG. 1, the hearing assist device 10, in this case depicted as a behind-the-ear hearing aid, has a housing 12 and includes a microphone 14, a digital signal processor ("DSP") 16 and a speaker (receiver) 18 with a sound outlet 20 directed into the patient's ear canal (not shown), powered by a replaceable or rechargeable battery 22, such as the hearing aids further disclosed in U.S. Pat. Nos. 7,519,193, 8,355,517, 8,358,797 and 8,767,987, all assigned to the assignee of the present invention and each incorporated by reference. The hearing aid 10 also includes an antenna/chipset 24 for receiving a wireless signal, which can preferably include control data 26, 28 and/or audio data 30 (such as from an audio streaming device) 32, and/or may alternatively receive control data 34 over a wired connection 36 or directly programmed or burned into the DSP 16.

As disclosed in U.S. Pat. No. 9,832,578, one source of the control data can be an audiologist's computer system 38, while an alternative source of control data can be the patient's computing device such as a smartphone 40. Smartphones have become ubiquitous in today's society, with many hearing aid owners also owning a smartphone. Assuming the smartphone and the hearing aid are so equipped, patients can wirelessly communicate with their hearing aids using their smartphone, such as using a Bluetooth or BLE signal, providing several advantages. The smartphone may have a touchscreen and control buttons which are larger than the switches or controls on the hearing aid itself, and the smartphone may be used to more easily enable patients, particularly elderly patients, to have the physical dexterity to adjust the hearing aid controls. The smartphone will have a display that the hearing aid lacks, so information from the hearing aid or control settings for the hearing aid can be presented on the smartphone display and be read by the patient. The smartphone will be connectable to one or more wide area networks, such as either or both of its cellphone network and the internet (including WiFi), enabling either the hearing aid manufacturer and/or an audiologist, remote from the hearing aid itself (but usually with the permission and participation of the hearing aid patient), to communicate information from or to the hearing aid. The audiologist thus may be able to remotely and timely perform services such as adjusting digital signal processor ("DSP") parameters so the hearing aid more properly adjusts the sound output for the hearing deficiency of that particular patient at that particular time and environmental location.

A perceived or actual shortcoming of many such systems is that they do not allow adequate protection over the hearing aid data of the patient. Possibilities exist for nefarious hacking into the system (possibly changing DSP parameters to the detriment of the patient), and/or for sensitive personalized data to be used or leaked outside the knowledge and/or permission of the patient. In Europe, for instance, stringent GDPR regulations have been put in place to allow citizens more control over their personalized data. Additionally, virus and malware problems run rampant when transmitting information over wide area networks such as the internet.

Owners of smartphones know that most smartphones include a camera, and that the camera can be used to input coded information to the smartphone, such as reading a bar code or a QR code (from Quick Response code). QR codes are commonly used on product packaging and promotional literature to direct consumers to a desired webpage. Bar codes and QR codes are limited in size. For instance, a QR code is limited to the number of bits in the QR display, such as a version 10 QR code, limited to exactly 57×57 pixels, e.g., about 1 kB or 3 kB of data are limits of common QR code sizes.

Hearing aid manufacturers are familiar with QR codes and their use on smartphones. For instance, hearing aid manufacturers may use a QR code on the packaging for a hearing aid, to quickly identify the type of hearing aid being purchased into the smartphone and/or for directing the patient's smartphone to a desired webpage for downloading of the correctly corresponding control software into the smartphone.

SUMMARY OF THE INVENTION

The present invention is method and system for communicating information between a computing device controlled by a hearing assist device patient and a different computer system controlled by a different party such as an audiologist, by using a visual computer code such as a bar code or more preferably a QR code. When the audiologist's computer system takes a picture of the QR code on the display of the patient's computing device, the QR code contains at least one piece of audiological data representing historical or current patient-specific usage of the hearing assist device. When the patient's computing device (such as a smartphone) takes a picture of the QR code on the display of the audiologist's computer system, the QR code contains audiological data, which the patient's computing device extracts to transmit instructions or information to adjust at least one audiological parameter setting on the patient's hearing assist device. Because the QR code is communicated visually, the patient can retain stringent control of his or her own audiological data. For certain patients, the QR code can be printed on paper and mailed from the audiologist to the patient. Alternatively, the patient in appropriate situations may transmit an image file of a QR code over a network, thereby communicating the same information with the audiologist. Because the QR code is limited in size, transmission of a virus or similar malware is impossible.

While the above-identified drawing figures set forth a preferred embodiment, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION OF THE PREFERRED EMBODIMENT(S)

The present invention involves two different software applications running on two different computing systems, in conjunction with a patient's hearing assist device(s) 10 such as one or a pair of hearing aids. Typically, one of the software applications will run on a patient's computing device such as a patient's smartphone 40. (As used herein, the possessive term "patient's" is not necessarily intended to mean ownership of the device, but rather use and control of the device regardless of actual ownership.) The patient's smartphone 40 can communicate with the patient's hearing aid(s) 10 over a wired connection or local area network (such as, most commonly, Bluetooth or BLE). Typically the other software application will run on a computer 38 controlled either by a hearing assist device manufacturer or audiologist. (As used herein, the possessive term "audiologist's" is not necessarily intended to mean ownership of the device, and is not limited to licensed audiologists, but rather use and control of the device by a desired person or entity (including fitting experts, manufacturers, etc.) other than the patient and regardless of actual ownership). The invention involves the way information from one software application is transmitted and/or imported into the other software application. The two related software apps can communicate patient-specific usage and/or hearing aid parameter setting information by a computer readable code such as a bar code or more preferably a QR code.

Figure 1:
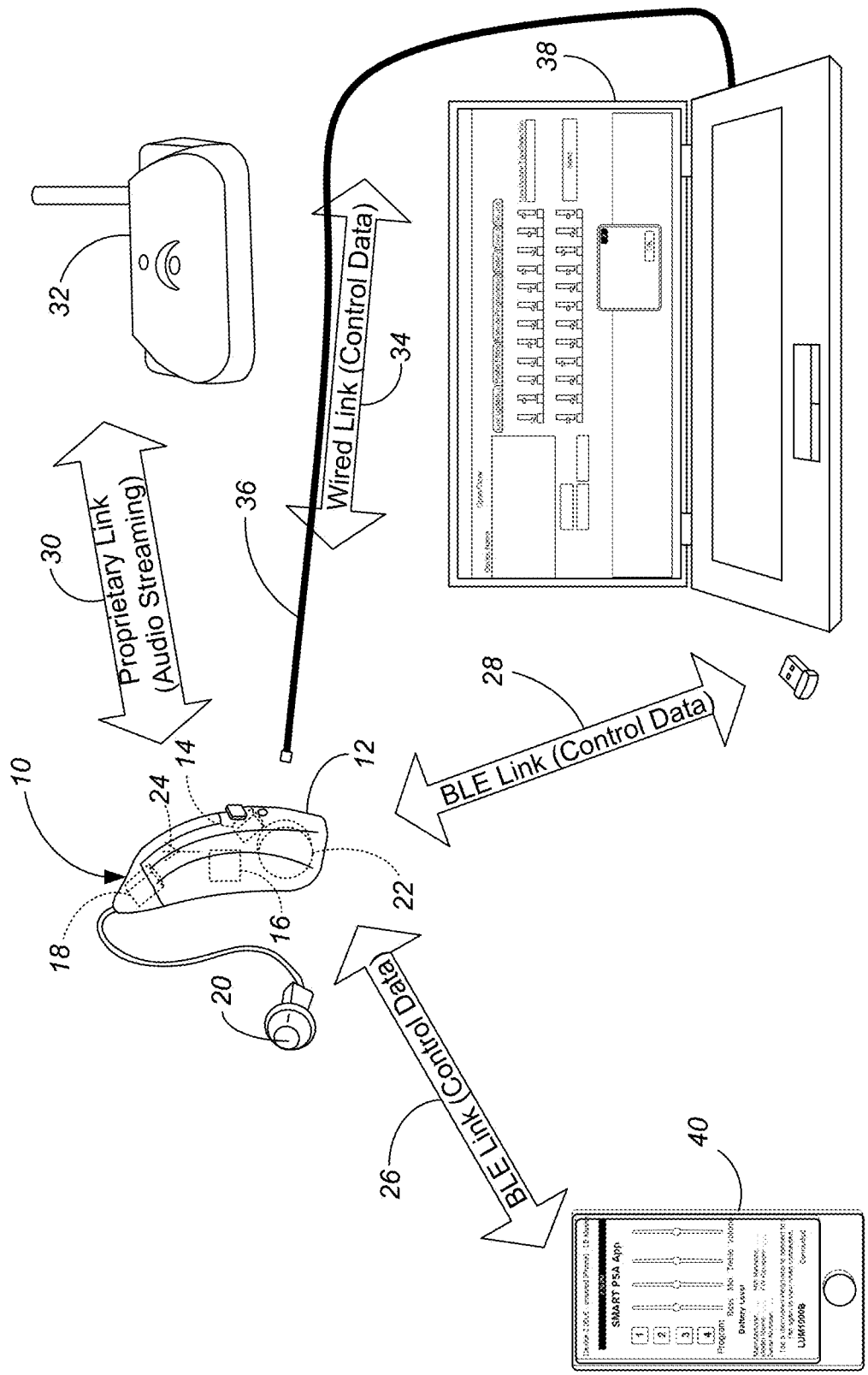
FIG. 1 is a schematic view showing prior art communication with a hearing aid in a system including a patient's smartphone and an audiologist's computer, such as disclosed in U.S. Pat. No. 9,832,578.
Figure 2:
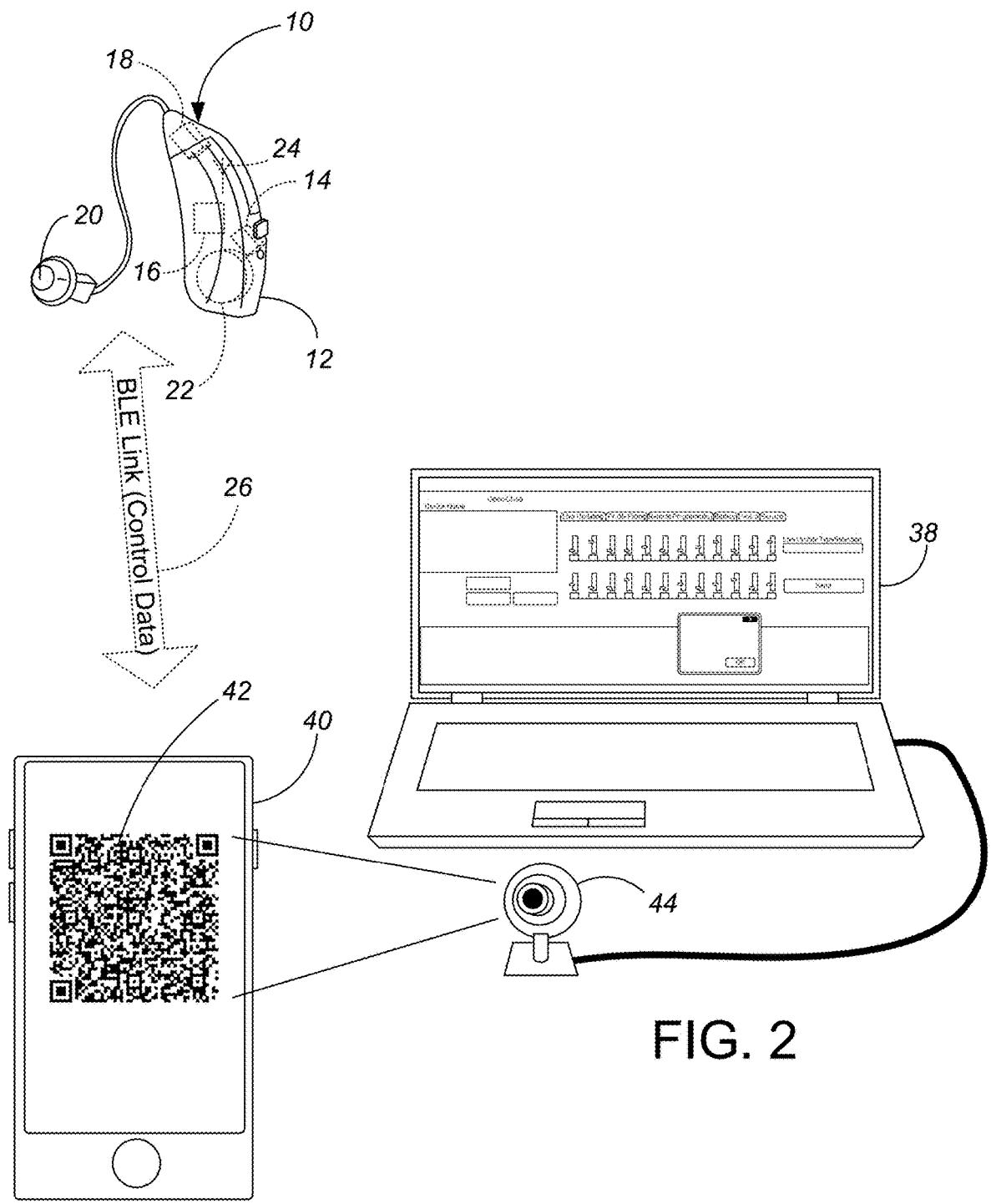
FIG. 2 is a schematic view of a preferred system in accordance with the present invention, using a QR code generated on a patient's smartphone to communicate hearing aid patient-personalized information to an audiologist's computer.
Figure 3:
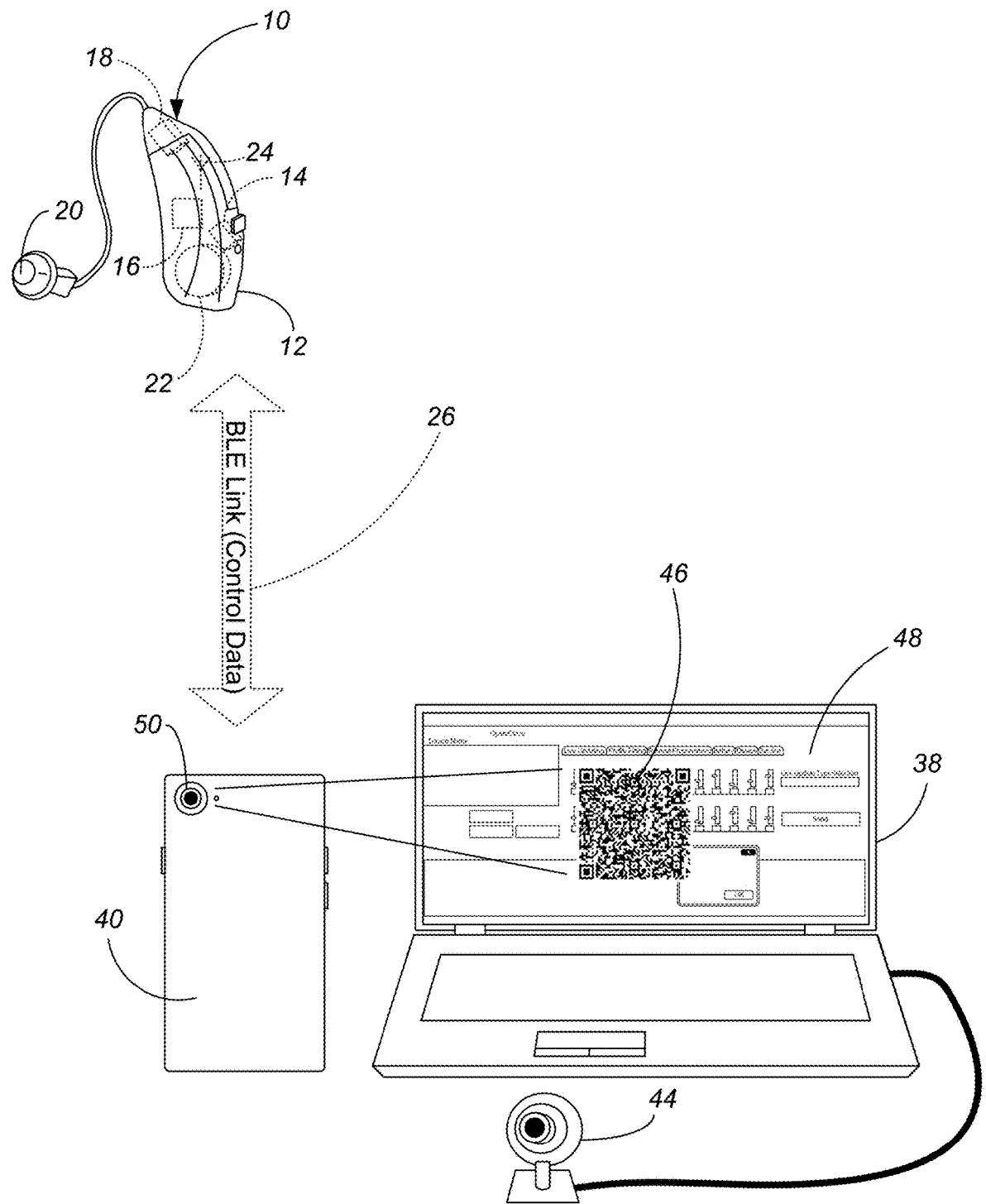
FIG. 3. is a schematic view of the preferred system of the present invention, using a QR code generated on an audiologist's computer to communicate hearing aid patient-personalized information to a patient's smartphone.

In the most secure application, the patient-specific hearing assist device audiological data is transmitted optically, from one display to the camera of the other computing device. FIGS. 2 and 3 thus show differing aspects of the present invention, which can be used alone or in conjunction with each other. In FIG. 2, a patient's smartphone 40, which either is currently or was previously in communication with the hearing aid 10, communicates information to the audiologist's computer system 38 using a visual code such as a QR code 42 or a bar code. The smartphone 40 generates a QR code 42 and displays the QR code 42 on its screen. At least part of the data in the generated QR code 42 is patient-specific audiological usage data for the hearing aid 10. The patient-specific audiological usage data could be originally derived within the hearing aid 10 and transmitted to the smartphone 40, or could be originally derived within the smartphone 40 during use of the hearing aid 10. The audiologist's computer system 38 uses a camera 44 to visually capture the code 42, with a processor (not separately shown) in the audiologist's computer 38 analyzing the captured image to interpret the QR code 42.

In FIG. 3, the audiologist's computer system 38 communicates information to the patient's computing device 40 using a visual code such as a QR code 46 or a bar code. The audiologist's computer system 38 generates a QR code 46 and displays the QR code 46 on its screen 48. At least part of the data in the generated QR code 46 is patient-specific audiological control data for adjusting the parameter settings within the hearing aid 10. The patient uses their smartphone camera 50 to take a photo or video of the QR code 46, visually importing the captured image of the QR code 46 so it can be analyzed with a processor (not separately shown) in the patient's smartphone 40 to interpret the QR code 46. The patient-specific audiological control data in the QR code 46 can then be converted into commands from the smartphone 40 to the hearing aid 10 to initially set up the hearing aid 10 for that particular patient, or to make adjustments at a later time to improve the hearing aid performance for that particular patient.

While the present invention is primarily expected to be used with the patient's smartphone 40, that is only because of their ubiquity and how commonly smartphone devices 40 include an acceptable camera 50 as well as the ability to download and use QR code reading and/or generating software. The patient's computing device could alternatively be a desktop, laptop or tablet computer, similarly equipped with a camera as part of the system and having the ability to interpret a QR code 46 visually captured by the camera and/or generate a QR code.

By communicating patient-specific audiological data optically, there is no possibility of intercepting or manipulation of any of the data by any third party, such as might occur via a transmission via the internet, or might even occur via a long range or short range wireless transmission. The patient and/or audiologist knows exactly when and where they are aiming the camera 44, 50 and taking a photo or video, and knows that the only data being communicated is information from the photo or video received by the camera 44, 50. With patient-specific audiological data being communicated only optically, the patient can maintain tight and stringent control over their own personal hearing aid data.

The QR code transfer scheme also very clearly limits the size of the transmission. Unlike virtually any other transmission scheme in use today, a QR code is limited to the number of bits in the QR display, such as about 1 kB or 3 kB of data in common QR code sizes. Once the size of the QR code is selected (such as a version 10 QR code, limited to exactly 57×57 pixels), no more data can be possibly transmitted. The use of a QR code is not only secure but is very transparent to the patient when information is being communicated with the fitting professional.

In the most preferred embodiment, communication between the smartphone 40 and the hearing aid 10 still occurs via a short range wireless transmission 26, such as using a BLE protocol. Because there is such a wireless transmission 26 in the system, there remains a possibility of some third party intercepting the wireless transmission 26 or of a third party device impersonating the smartphone 40 to deliver false setting parameter information or steal the usage data coming from the hearing aid 10. In general, this risk is considered remote and insignificant, because appropriate secure pairing between the smartphone 40 and the hearing aid 10 can be required, with the patient selecting a secure location and time to initiate such communication between the smartphone 40 and the hearing device 10. Additionally, the QR codes 42, 46 can be encrypted, greatly increasing the difficulty of tampering with the QR code. For even more secure control of patient data, communications between the smartphone 40 and the hearing device 10 could be restricted to wired communications.

Figure 4:
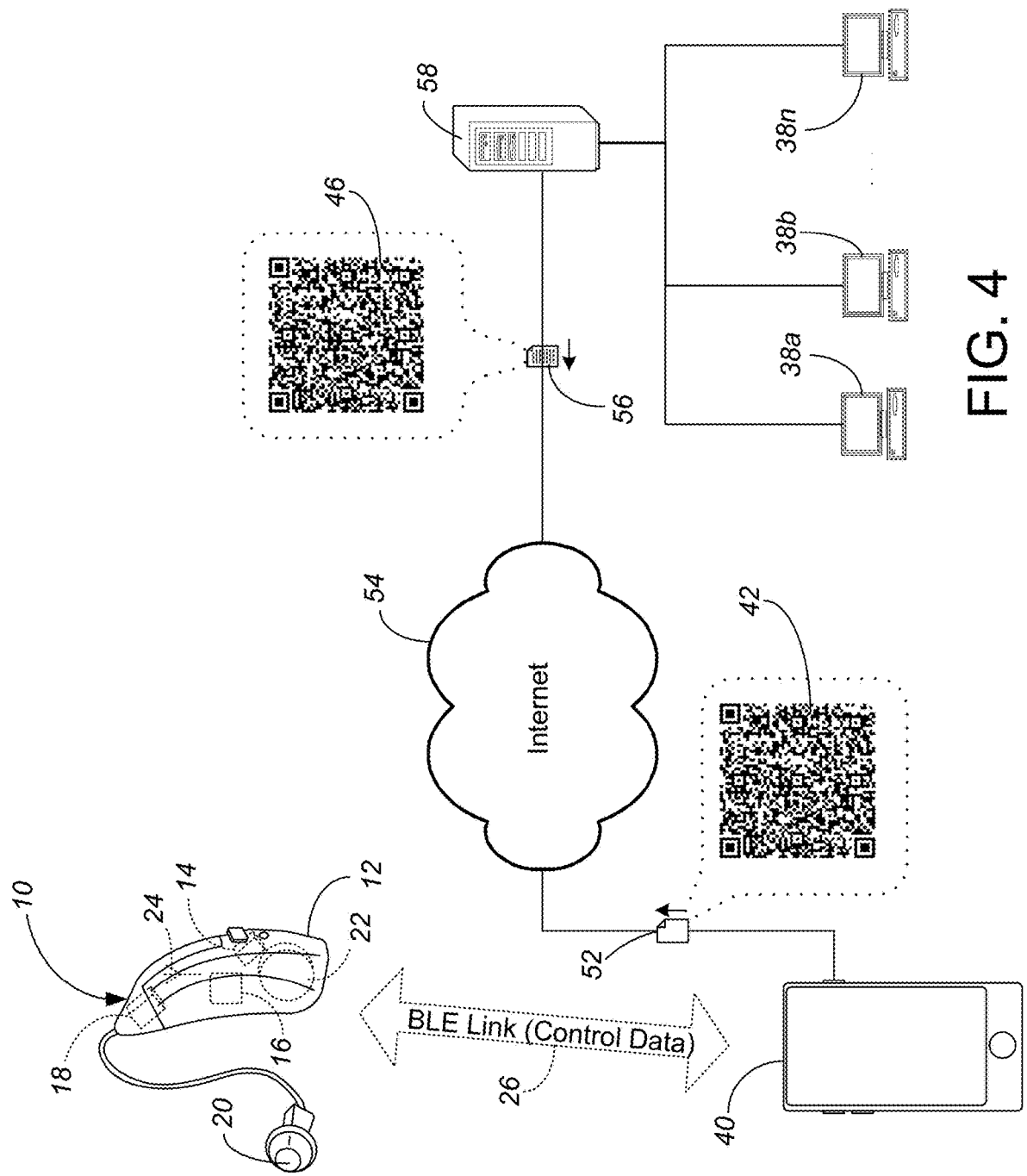
FIG. 4 is a schematic view of the preferred system of the present invention, showing two way communication between an audiologist datacenter and a patient's smartphone, using internet-transmitted QR codes.

FIG. 4 depicts situations where the benefits of a longer distance transmission outweigh the need for absolute security. An extremely secure transfer of information can be achieved by transmitting a photo or computer-generated image file (such as a .jpg file) of an encrypted QR code, such as through an email or text message. FIG. 4 thus shows the smartphone 40 transmitting an image file 52 of an encrypted QR code 42 through the internet 54, which QR code 42 includes patient-specific audiological usage data for the hearing aid 10. FIG. 4 also shows the audiologist's computer 38a, 38b, 38n transmitting an image file 56 of an encrypted QR code 46 through the internet 54, which QR code 46 includes patient-specific audiological control data for adjusting the DSP parameter settings within the hearing aid 10. The smartphone 40 receives the image file 56 and interprets the QR code 46, thereafter transmitting the DSP parameter setting adjustment to the hearing device 10. The embodiment shown in FIG. 4 allows the patient to determine whether and when to accept the risk of .jpg file transmission versus the need to bring the patient's computing device 40 within the several feet of the audiologist's computing device 38 required for optical/camera transmission of the QR code information. The use of a QR code 42, 46 to transmit information between the audiologist's software application and the patient's software application, whether by limited distance optical (taking a photo or video, as shown in FIGS. 2 and 3) or longer distance other (email or text message, as shown in FIG. 4) means that in all cases the information imported into the application is limited to the size of the QR code 42, 46, making transmission of a virus or similar malware impossible.

FIG. 4 also demonstrates another aspect of the preferred embodiment, that when transmitting the QR code image file 52, 56 over a wide area network 54 to a remote location, the audiologist's computer 38 can be any one of numerous audiologist's computers 38a, 38b, 38n, such as at a central datacenter connected to either a secure server 58 or a secure cloud database. Such an arrangement allows a patient, at any time (day or night, 24/7), to transmit usage information and/or receive hearing aid parameter setting adjustments for a professional solution to combat any emergency problem being faced by the patient and correct hearing aid performance in any particular environment at any particular time.

One of the pieces of information which is within the QR code 42, 46 is identifying information for the particular hearing aid 10. For instance, "MDA" information which is manufacturer specific information, including a device serial number, can be transmitted in a 288 byte section of the QR code 42, 46. The two applications perform a confirmation that sender and receiver are both correspondingly matched to the particular hearing device 10. For example, a wife with the same type of hearing aid as her husband is not able to mistakenly use the software application to connect with her husband's hearing aid(s) by accident. Such wrong connections are also prevented in larger groups, such as if multiple students in a class or multiple people in a home or apartment have similarly programmable hearing assist devices.

Another section of information transmitted by QR code 42, 46 is programming information for the hearing device 10. For example, the data (not including the English language portions) of a file known as a "PGM" file is used for hearing aids from IntriCon Corporation, assignee of the present invention, can be sent in a 528 byte section of the QR code 42, 46. When included in the QR code 42 from the patient's smartphone 40, the programming information is usage information, telling the audiologist the current or previous DSP parameter settings for the hearing aid 10. When included in the QR code 46 from the audiologist's computer 38, the programming information is future DSP parameter settings for the hearing aid 10, telling the smartphone 40 how to adjust the hearing aid 10 for better audio output for a particular patient/time/environment.

An important aspect of the preferred software applications is that that the patient is in control of his or her own data. There is no linkage or hidden push notifications or responses from the patient's software application to either the cloud server or to the audiologist's software application. The only way in which the patient software application outputs information is through generation of a QR code 42. It is then the patient's sole decision as to whether and when to provide the patient-generated QR code 42 to a professional, vendor, etc.

Visually transferring data from the audiologist to the patient's computing device 40 via QR code ensures there is no possibility of tampering with the data values. It is again the patient's sole decision as to whether and when to acquire (i.e., take a photo or video of) the audiologist-generated QR code 46 and make changes to the DSP parameter settings of his or her own hearing aid(s) 10. The patent-specific QR code 46 could be printed, and delivered to the patient by hand, by mail or by other common carrier, with the patient taking a photo or video of the QR code 46 at a later time after generation and printing. An image file of the QR code 46 could alternatively be transmitted via email, text message or other electronic transfer, which provides similar security benefits but is not quite as absolutely-tamper-proof as visual transmission into the patient's computing device camera 50. Mail delivery of the printed patient-specific QR code 46 is considered less tamper-proof than an image file transmission, and is particularly beneficial for remote patients who may not have access to email, text message or other electronic transfer.

The present invention allows the patient to store multiple QR codes 46 from the audiologist as image files within the memory of the smartphone 40. For instance, a patient may recall a prior problematic acoustic environment (such as eating in a particular restaurant), when the patient reported a problem to the audiologist and the audiologist provided a set of DSP parameter settings customized for that particular patient when in that particular acoustic environment. The patient can then search the photos stored on the smartphone 40 (organized according to the image file metadata), looking for a photo of a QR code from that remembered date or looking for a photo of a QR code recorded at that remembered location. Once identifying the image file with the desired QR code, the patient can, within the software app, have the smartphone 40 initiate appropriate changes to the DSP parameter settings within the hearing aid(s) 10 for use on returning to the restaurant.

In some embodiments, the preferred QR code generators, used in both the patient's smartphone 40 and in the audiologist's computer system 38, can adaptively select the size of the QR code 42, 46 based upon the amount of data that is desired to be transmitted.

The QR code data preferably includes information to adjust hearing aid functions, settings and adjustments. For instance, the most preferred QR-code 46 generated by the audiologist transfers up to 3 kB of data to the patient's smartphone 40, including fields of information for:

a) Deprivation (points);

b) serial number or similar identifying information of the patient's hearing assist device(s) 10 (for the patient's smartphone 40 to verify and ensure that the programming settings are not input into the wrong hearing assist device);

c) a simplified set of instructions for DSP parameter settings, such as one of any of twenty-four or thirty-two common DSP parameter setting categories that adequately cover the vast majority of hearing deficiencies, each category having its own value known by either the smartphone 40 or hearing aid 10 for overall pre-amplifier gain, compression ratios, thresholds and output compression limiter (MPO) settings for each of eight channels, time constants, noise reduction, matrix gain, equalization filter band gain settings for each of twelve different frequency bands, and adaptive feedback canceller on/off. Other embodiments can include a full set of parameter settings for the particular DSP amplifier and hearing aid being used.

In more particularity, when used in conjunction with a hearing aid using an AUDION 16 DSP with sixteen frequency bands from IntriCon Corporation, the QR code can include the following fields and relative sizes of data:

Example 1

```
{
    "id":"<string>",
    "version":"1",
    "right": {
        "serial":"<string>",
        "configuration":"<base64>",
        "program0":"<base64>",
        "program1":"<base64>",
        "program2":"<base64>",
        "program3":"<base64>",
        "program4":"<base64>",
        "program5":"<base64>",
        "mda7":"<base64>",
        "mda8":"<base64>",
        "mda9":"<base64>",
        "mda10":"<base64>",
        "biquad11":"<base64>",
        "biquad12":"<base64>"
```

-continued

```
    },
    "left":
    {
        "serial":"<string>",
        "configuration":"<base64>",
        "program0":"<base64>",
        "program1":"<base64>",
        "program2":"<base64>",
        "program3":"<base64>",
        "program4":"<base64>",
        "program5":"<base64>",
        "mda7":"<base64>",
        "mda8":"<base64>",
        "mda9":"<base64>",
        "mda10":"<base64>",
        "biquad11":"<base64>",
        "biquad12":"<base64>"
    }
}
```

TABLE 1

| Key Name | Value Length (characters) | Description |
| --- | --- | --- |
| [Header] | | |
| id | variable | Identifier for the data. |
| version | variable | Format version. |
| left | 102-482 | The data for the left hearing aid. |
| right | 102-482 | The data for the right hearing aid. |

| Key Name | Length (characters) | Description |
| --- | --- | --- |
| [left/right] | | |
| serial | 10 | The serial number of the hearing aid. |
| configuration | 16 | Parameters that apply to the entire hearing aid. 64-bit encoded. |
| program0 | 76 | Program specific parameters. 64-bit encoded. |
| program1 | 76 | Program specific parameters. 64-bit encoded. |
| program2 | 76 | Program specific parameters. 64-bit encoded. |
| program3 | 76 | Program specific parameters. 64-bit encoded. |
| program4 | 76 | Program specific parameters. 64-bit encoded. |
| program5 | 76 | Program specific parameters. 64-bit encoded. |
| mda7 | 80 | Parameters that apply to the entire hearing aid. 64-bit encoded. |
| mda8 | 80 | Parameters that apply to the entire hearing aid. 64-bit encoded. |
| mda9 | 80 | Parameters that apply to the entire hearing aid. 64-bit encoded. |
| mda10 | 80 | Parameters that apply to the entire hearing aid. 64-bit encoded. |
| biquad11 | 56 | Parameters that apply to the entire hearing aid. 64-bit encoded. |
| biquad12 | 56 | Parameters that apply to the entire hearing aid. 64-bit encoded. |

| Key Name | Length (bits) after 64-bit decoding | Description |
| --- | --- | --- |
| [configuration] | | |
| SW Mode | 2 | Configures the physical type of program change switch used by the instrument. |
| VC_Mode | 2 | Configures the physical volume control type used by the instrument. |
| VC EN | 1 | Enables and disables the physical volume control on the instrument. |
| VC Prompt mode | 3 | Sets the type of prompts are to be sounded when the volume control is changed. |

TABLE 1-continued

| | | |
|---|---|---|
| PGM Prmpt | 2 | Sets the type of prompts are to be sounded when the program is changed. |
| WRN Prmpt | 2 | What type of prompts are to be sounded when for warnings, such as low battery. |
| VC_Startup | 5 | The default VC level at start up |
| PGM_Startup | 3 | Sets the program to start up in when the instrument powers on. |
| VC NumSteps | 3 | Configures how many steps the volume control range is to have. |
| VC Step Size | 3 | Configures the decibel size each volume control change will change. |
| VC_Analog_Range | 3 | Configures the volume control range when VC_Mode is set to Analog VC. For Analog VC, the number of steps is always 31 (32 VC positions: 0 to 31). Divide VC_Analog_Range by 31 to get the step size. |
| Nbr_of_Prgms | 3 | Configures how many programs the instrument will have. |
| Tone Level | 3 | N/A |
| Tone Frequency | 3 | Frequency to use by any prompts set to tones. |
| T Ref | 1 | N/A |
| Dir Spacing | 3 | The physical acoustic distance between the two microphones when the instrument input mux is set to a directional mode. |
| Dir Mic Calibration | 5 | Mic calibration adjustment for directional microphone options when 2 microphones are used. Use in conjunction with Dir_Mic_Cal_Input. |
| Cal_Input | 1 | Selects which microphone input to apply the Dir_Mic_Cal adjustment to. |
| AD Sens | 2 | Adaptive Directional Sensitivity |
| ATC | 1 | Auto Telecoil |
| Tap Mode | 2 | ACOUSTAP ™ Mode |
| Tap Sensitivity | 2 | Adjusts the sensitivity of the ACOUSTAP ™ acoustic program change switch. This will generally be used in "normal" mode. Only set on "High" when using microphones that have a built-in low frequency roll-off. |
| Power On Level | 2 | This sets the volume level the instrument will be at until the Power On Delay finishes. |
| Power On Delay | 2 | Power On Delay sets how long the instrument remains at Power_On_Level before it changes to normal volume. |
| Noise Level | 3 | Level of the noise generator when input mux is set to noise generator. |
| HP Enable | 1 | High Power Mode parallels two output stages to provide more output power to aids with lower impedance. |
| A. Save | 1 | Auto Save: If the Volume Control Power on Position and Power On Program should be automatically saved or depend on the configuration settings. |
| Noise_Fit_1_preset | 3 | Noise Filter 1 |
| Noise_Fit_2_preset | 3 | Noise Filter 2 |
| Out_Fit_2_index | 3 | Output Filter 2 |
| Out_Fit_1_index | 3 | Output Filter 1 |
| O_F_EN | 1 | Output Filter Enable |
| N_Ref | 1 | This sets the noise generator to be input referred or output referred. When the Noise Generator is output referred, the Noise Generator shape is only affected by the Noise Filters below. When the Noise Generator is input referred, the Noise Generator Filters are disabled and all other program parameters (BEQs, compression, etc.) affect the shape of the noise. |
| Reserved [program0-5] | 18 | N/A |
| IN_MODE_P1 | 4 | Input Mux |
| PAG_P0 | 4 | Analog Preamp Gain |
| PAG_P1 | 4 | Analog Preamp Gain |
| PADG_P1 | 2 | Digital Preamp Gain |
| PADG_P2 | 2 | Digital Preamp Gain |
| MGMAN_P1 | 3 | Matrix Gain Mantissa |
| MGEXP_P1 | 3 | Matrix Gain Exponent |
| FB | 2 | Feedback Canceller |
| NR | 3 | Noise Reduction |
| LL EXP | 1 | Low Level Expansion |
| Wind | 1 | Wind Suppression |
| Reserved | 3 | N/A |
| BEQ1 | 5 | Band Gain |
| BEQ2 | 5 | Band Gain |
| BEQ3 | 5 | Band Gain |
| BEQ4 | 5 | Band Gain |
| BEQ5 | 5 | Band Gain |
| BEQ6 | 5 | Band Gain |
| Reserved | 2 | N/A |
| BEQ7 | 5 | Band Gain |
| BEQ8 | 5 | Band Gain |
| BEQ9 | 5 | Band Gain |
| BEQ10 | 5 | Band Gain |
| BEQ11 | 5 | Band Gain |
| BEQ12 | 5 | Band Gain |
| Reserved | 2 | N/A |
| BEQ13 | 5 | Band Gain |
| BEQ14 | 5 | Band Gain |
| BEQ15 | 5 | Band Gain |
| BEQ16 | 5 | Band Gain |
| CR1 | 6 | Compression Ratio |
| CR2 | 6 | Compression Ratio |
| CR3 | 6 | Compression Ratio |
| CR4 | 6 | Compression Ratio |
| CR5 | 6 | Compression Ratio |
| CR6 | 6 | Compression Ratio |
| CR7 | 6 | Compression Ratio |
| Reserved | 2 | N/A |
| CR8 | 6 | Compression Ratio |
| CR9 | 6 | Compression Ratio |
| CR10 | 6 | Compression Ratio |
| CR11 | 6 | Compression Ratio |
| CR12 | 6 | Compression Ratio |
| Reserved | 2 | N/A |
| CR13 | 6 | Compression Ratio |
| CR14 | 6 | Compression Ratio |
| CR15 | 6 | Compression Ratio |
| CR16 | 6 | Compression Ratio |
| compress_consts_1 | 4 | Compression Time Constants |
| compress_consts_2 | 4 | Compression Time Constants |
| compress_consts_3 | 4 | Compression Time Constants |
| compress_consts_4 | 4 | Compression Time Constants |
| compress_consts_5 | 4 | Compression Time Constants |
| compress_consts_6 | 4 | Compression Time Constants |
| compress_consts_7 | 4 | Compression Time Constants |
| compress_consts_8 | 4 | Compression Time Constants |
| compress_consts_9 | 4 | Compression Time Constants |
| compress_consts_10 | 4 | Compression Time Constants |
| compress_consts_11 | 4 | Compression Time Constants |
| compress_consts_12 | 4 | Compression Time Constants |
| compress_consts_13 | 4 | Compression Time Constants |
| compress_consts_14 | 4 | Compression Time Constants |
| compress_consts_15 | 4 | Compression Time Constants |
| compress_consts_16 | 4 | Compression Time Constants |
| Comp_TK_1 | 5 | Compression Threshold |
| Reserved | 3 | N/A |
| Comp_TK_2 | 5 | Compression Threshold |
| Comp_TK_3 | 5 | Compression Threshold |
| Comp_TK_4 | 5 | Compression Threshold |

TABLE 1-continued

| Name | Bits | Description |
|---|---|---|
| Comp_TK_5 | 5 | Compression Threshold |
| Comp_TK_6 | 5 | Compression Threshold |
| Comp_TK_7 | 5 | Compression Threshold |
| Reserved | 2 | N/A |
| Comp_TK_8 | 5 | Compression Threshold |
| Comp_TK_9 | 5 | Compression Threshold |
| Comp_TK_10 | 5 | Compression Threshold |
| Comp_TK_11 | 5 | Compression Threshold |
| Comp_TK_12 | 5 | Compression Threshold |
| Comp_TK_13 | 5 | Compression Threshold |
| Reserved | 2 | N/A |
| Comp_TK_14 | 5 | Compression Threshold |
| Comp_TK_15 | 5 | Compression Threshold |
| Comp_TK_16 | 5 | Compression Threshold |
| MPO_TK_1 | 4 | Maximum Power Output Threshold |
| MPO_TK_2 | 4 | Maximum Power Output Threshold |
| MPO_TK_3 | 4 | Maximum Power Output Threshold |
| MPO_TK_4 | 4 | Maximum Power Output Threshold |
| Reserved | 1 | N/A |
| MPO_TK_5 | 4 | Maximum Power Output Threshold |
| MPO_TK_6 | 4 | Maximum Power Output Threshold |
| MPO_TK_7 | 4 | Maximum Power Output Threshold |
| MPO_TK_8 | 4 | Maximum Power Output Threshold |
| MPO_TK_9 | 4 | Maximum Power Output Threshold |
| MPO_TK_10 | 4 | Maximum Power Output Threshold |
| MPO_TK_11 | 4 | Maximum Power Output Threshold |
| MPO_TK_12 | 4 | Maximum Power Output Threshold |
| MPO_TK_13 | 4 | Maximum Power Output Threshold |
| MPO_TK_14 | 4 | Maximum Power Output Threshold |
| MPO_TK_15 | 4 | Maximum Power Output Threshold |
| MPO_TK_16 | 4 | Maximum Power Output Threshold |
| MPO_atk_1 | 3 | Maximum Power Output Attack |
| MPO_Rel_1 | 3 | Maximum Power Output Release |
| Reserved | 1 | N/A |
| remote mix ratio | 4 | When the Input is set to a Streaming input, this parameter controls the volume of the microphone on the hearing instrument in relation to the level of the Companion Microphone Accessory. |
| Low Cut Input Filter | 4 | This is a low-cut filter offering a selection of 3 dB down cutoff frequencies. |
| [biquad11] | | |
| Noise_Filter1_A0 | 24 | These are biQuad coefficients for the first noise filter. |
| Reserved | 8 | N/A |
| Noise_Filter1_A1 | 24 | These are biQuad coefficients for the first noise filter. |
| Reserved | 8 | N/A |
| Noise_Filter1_A2 | 24 | These are biQuad coefficients for the first noise filter. |
| Reserved | 8 | N/A |
| Noise_Filter1_B1 | 24 | These are biQuad coefficients for the first noise filter. |
| Reserved | 8 | N/A |
| Noise_Filter1_B2 | 24 | These are biQuad coefficients for the first noise filter. |
| Reserved | 8 | N/A |
| Noise_Filter2_A0 | 24 | These are biQuad coefficients for the second noise filter. |
| Reserved | 8 | N/A |
| Noise_Filter2_A1 | 24 | These are biQuad coefficients for the second noise filter. |
| Reserved | 8 | N/A |
| Noise_Filter2_A2 | 24 | These are biQuad coefficients for the second noise filter. |
| Reserved | 8 | N/A |
| Noise_Filter2_B1 | 24 | These are biQuad coefficients for the second noise filter. |
| Reserved | 8 | N/A |
| Noise_Filter2_B2 | 24 | These are biQuad coefficients for the second noise filter. |
| Reserved | 8 | N/A |
| [biquad12] | | |
| Output_Filter1_A0 | 24 | These are biQuad coefficients for the first output filter. |
| Reserved | 8 | N/A |
| Output_Filter1_A1 | 24 | These are biQuad coefficients for the first output filter. |
| Reserved | 8 | N/A |
| Output_Filter1_A2 | 24 | These are biQuad coefficients for the first output filter. |
| Reserved | 8 | N/A |
| Output_Filter1_B1 | 24 | These are biQuad coefficients for the first output filter. |
| Reserved | 8 | N/A |
| Output_Filter1_B2 | 24 | These are biQuad coefficients for the first output filter. |
| Reserved | 8 | N/A |
| Output_Filter2_A0 | 24 | These are biQuad coefficients for the second output filter. |
| Reserved | 8 | N/A |
| Output_Filter2_A1 | 24 | These are biQuad coefficients for the second output filter. |
| Reserved | 8 | N/A |
| Output_Filter2_A2 | 24 | These are biQuad coefficients for the second output filter. |
| Reserved | 8 | N/A |
| Output_Filter2_B1 | 24 | These are biQuad coefficients for the second output filter. |
| Reserved | 8 | N/A |
| Output_Filter2_B2 | 24 | These are biQuad coefficients for the second output filter. |
| Reserved | 8 | N/A |
| [mda7] | | |
| Platform ID | 16 | Platform Identification differentiates DSP hybrids from each other. The Generic Driver provides an amp type differentiator that simplifies this. Platform ID remains useful for determining if different amp types are under the same platform. |
| Reserved | 16 | N/A |
| Reserved | 8 | N/A |
| Reserved | 8 | N/A |
| Reserved | 8 | N/A |
| Ear | 2 | Left/right side. |
| Reserved | 6 | N/A |
| MANF ID | 12 | Manufacturer Identification is a security feature. If this is set to a non-zero value the amplifier cannot be read or written by any software unless the pass code to activate the manufacturer ID has been entered in the security section of the software. |
| LayoutVersion | 4 | Layout Version is meant to track the Structure of the MDA_x memory space. Use as desired. This allows upgrades of this memory without complicated decoding algorithms. If you change the layout of this memory your software can simply read this version and act accordingly. |
| Model ID | 16 | Used to store the Model Identification number (Model ID). Hardware options are specific to a Model ID. Options include microphone, receiver, and volume control. The Model ID allows software applications to know which hardware options to display. |
| SN | 8 | Two characters of the serial number. |
| SN | 8 | Two characters of the serial number. |
| SN | 8 | Two characters of the serial number. |
| SN | 8 | Two characters of the serial number. |

TABLE 1-continued

| SN | 8 | Two characters of the serial number. |
|---|---|---|
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| MDA | 8 | Manufacture's Data |
| [mda8/9/10] | | |
| Reserved | 1920 | N/A |

In preferred embodiments, the order of the key-value pairs in this data is not important. While these data fields and lengths are appropriate for transmitting DSP parameter values to IntriCon's hearing aids using AUDION 16 DSP amplifiers, other data lengths and potentially other sets of parameters could be sent to a hearing aid using a different DSP.

d) map settings for adaptive finetuning of the DSP parameter settings listed in c) above;

e) Date and time of creating the QR code 46 (this enables the patient's smartphone 40 to compare the date and/or time information from the newly received QR code 46 to date and/or time information of existing audiological parameter settings on the patient's hearing assist device, allowing the patient to keep the most updated DSP parameter settings in the hearing aid 10 and/or consciously and knowingly return to an earlier set of DSP parameter settings);

f) Software version; and g) recommended max input levels (real time).

In alternative embodiments, the data contained in the audiologist-generated QR code 46 includes different fields and different information, including both additional information and subsets of this information.

The most preferred QR code 42 generated by the patient's application for transferring information to the audiologist's computing device 38 includes information (up to 3 kb or more) for transferring:

a) customer number and/or serial number or similar identifying information of the patient's hearing assist device (s) 10 (for the audiologist to verify which customer and which hearing aid is at issue, possibly referencing a database showing that patient's hearing test results and that patient's history of making DSP parameter setting changes and/or that patient's history of performing cognitive training exercises);

b) Time stamp of program settings (training sessions) with time and action like a log file, advising the audiologist of whether the patient performed various sessions prescribed by the audiologist for the patient's cognitive development using the hearing aid;

c) Connection time, advising the audiologist of when the hearing aid was used and the source of audio content during that time period;

d) Acoustic environment levels over time (exceeding recommendation) of the microphone audio input, with time and date (this could alternative include more detailed historical acoustic information, such as noise, frequency, etc., such as percentile weighted input noise and speech levels per Channel);

e) Percentile Real time analyses data (sum signal or recorded period of time);

f) Date and time of using the "complain button" including acoustic environment data, i.e., patient can mark/record different acoustic situations where the hearing aid is not adequately performing, so the audiologist can program a set of DSP parameter settings better suited for similar acoustic situations;

g) a simplified set of currently-being-used DSP parameter settings, such as one of any of twenty-four or thirty-two common DSP parameter setting categories that adequately cover the vast majority of hearing deficiencies, each category having its own value known by the audiologist or the audiologist's computer 38 for overall pre-amplifier gain, compression ratios, thresholds and output compression limiter (MPO) settings for each of eight channels, time constants, noise reduction, matrix gain, equalization filter band gain settings for each of twelve different frequency bands, and adaptive feedback canceller on/off. This can include any or all of the DSP parameters listed above in Example 1 and Table 1, or additional information. This can also include a log file of adjustments to audiological parameter settings on the patient's hearing assist device 10 made by the patient using his or her smartphone 40; and h) map settings for adaptive finetuning of the DSP parameter settings listed in g) above;

The audiologist can thus read the usage data pertaining to the hearing aid 10 from the patient's smart device 40. With this information, the audiologist can better adjust hearing device settings to gain better results. In alternative embodiments, the data contained in the patient-generated QR code 42 includes different fields and different information, including both additional information and subsets of this information.

Although the present invention has been described with reference to preferred embodiments, workers skilled in the art will recognize that changes may be made in form and detail without departing from the spirit and scope of the invention.

The invention claimed is:

1. A method for fitting a hearing assist device for a patient, comprising:

storing a plurality of images of computer readable codes on the patient's computing device, each of the computer readable codes containing:
        a) identifying information for the patient's hearing assist device; and
        b) patient-specific hearing assist device audiological data;
    displaying one of the plurality of images on the patient's computing device;
    with a camera on a patient's computing device, acquiring an image of the displayed computer readable code;
    processing the image on the patient's computing device to extract both the identifying information and at least one piece of audiological data;
    verifying that the identifying information in the computer readable code matches the particular hearing assist device; and
    only if a match is verified, transmitting instructions or information from the patient's computing device to the patient's hearing assist device based on the extracted audiological data, thereby adjusting at least one audiological parameter setting on the patient's hearing assist device.

2. The method of claim 1, wherein the computer readable code is a quick response (QR) code.

3. The method of claim 1, wherein the computer readable code comprises date and/or time information for when the computer readable code was generated, and further comprising:
comparing the date and/or time information from the computer readable code to date and/or time information of existing audiological parameter settings on the patient's hearing assist device.

4. The method of claim 3, comprising comparing the date and/or time information from two different computer readable codes, and alerting the patient if the adjustment involves replacing newer audiological parameter settings with older audiological parameter settings.

5. The method of claim 1, further comprising:
at a separate time on a patient's computing device, acquiring a digital image file of a second computer readable code over a wide area network connection;
processing the digital image file on the patient's computing device to extract at least one piece of second audiological data; and
transmitting instructions or information from the patient's computing device to the patient's hearing assist device based on the extracted second audiological data, thereby making a second adjustment of at least one audiological parameter setting on the patient's hearing assist device.

6. The method of claim 1, further comprising:
with a display on a patient's computing device, displaying patient-specific hearing assist device audiological usage data in a computer readable code.

7. A method for fitting a hearing assist device for a patient, comprising:
displaying patient-specific hearing assist device audiological data in a first computer readable code;
with a camera on a patient's computing device, acquiring an image of the displayed first computer readable code;
processing the image on the patient's computing device to extract at least one piece of audiological data; and
transmitting instructions or information from the patient's computing device to the patient's hearing assist device based on the extracted audiological data, thereby adjusting at least one audiological parameter setting on the patient's hearing assist device; and
further involving assessing usage of the hearing assist device comprising:
displaying patient-specific hearing assist device audiological usage data in a second computer readable code on the patient's computing device;
with a camera, acquiring an image of the displayed second computer readable code;
processing the image of the displayed second computer readable code to extract at least one piece of audiological data representing patient-specific usage of the hearing assist device.

8. The method of claim 7, wherein the computer readable code comprises identifying information for the patient's hearing assist device, and further comprising:
verifying that the identifying information in the computer readable code matches the particular hearing assist device.

9. The method of claim 7, further comprising:
storing a plurality of images of computer readable codes on the patient's computing device.

10. The method of claim 7, wherein the second computer readable code is a quick response (QR) code.

11. The method of claim 7, wherein the second computer readable code comprises identifying information for the patient and/or patient's hearing assist device.

12. The method of claim 11, wherein the audiological data representing patient-specific usage comprises a log file of training sessions performed by the patient.

13. The method of claim 11, wherein the audiological data representing patient-specific usage comprises a log file of adjustments to audiological parameter settings on the patient's hearing assist device made by the patient.

14. The method of claim 11, wherein the audiological data representing patient-specific usage comprises a file of audio environmental data associated with complaint instances.

15. The method of claim 7, further comprising:
at a separate time on a patient's computing device, transmitting a digital image file of a third computer readable code over a wide area network connection;
processing the transmitted digital image file to extract at least one second piece of audiological data representing patient-specific usage of the hearing assist device.

16. A method for fitting a hearing assist device for a patient, comprising:
displaying patient-specific hearing assist device audiological data in a computer readable code;
with a camera on a patient's computing device, acquiring an image of the displayed computer readable code;
processing the image on the patient's computing device to extract at least one piece of audiological data; and
transmitting instructions or information from the patient's computing device to the patient's hearing assist device based on the extracted audiological data, thereby adjusting at least one audiological parameter setting on the patient's hearing assist device;
the method performed in a system comprising an audiologist's computing system having an audiologist's display controlled by a system processor, the audiologist's computing system not being able to remotely configure the patient's hearing assist device without the permission of the patient,
the method further comprising using the system processor to generate the computer readable code with patient-specific hearing assist device audiological data therein;
wherein the audiologist's computing system comprises an audiologist's camera,
the method further comprising using the audiologist's camera to acquire a second computer readable code.

17. The method of claim 16, wherein the computer readable code is transmitted as a digital image over a wide area network connection.

* * * * *